(12) United States Patent
Saha et al.

(10) Patent No.: US 8,487,621 B2
(45) Date of Patent: Jul. 16, 2013

(54) RADIO FREQUENCY (RF) COIL FOR MRI HAVING HIGH THERMAL CONDUCTIVITY

(75) Inventors: Saikat Saha, Florence, SC (US); Longzhi Jiang, Florence, SC (US); Timothy John Havens, Florence, SC (US)

(73) Assignee: General Electric Company, Schenectady, NY (US)

( * ) Notice: Subject to any disclaimer, the term of this patent is extended or adjusted under 35 U.S.C. 154(b) by 403 days.

(21) Appl. No.: 12/881,375

(22) Filed: Sep. 14, 2010

(65) Prior Publication Data

US 2012/0062231 A1  Mar. 15, 2012

(51) Int. Cl.
*G01V 3/00* (2006.01)
(52) U.S. Cl.
USPC .......................................................... 324/318
(58) Field of Classification Search
USPC ................................................. 324/300–322
See application file for complete search history.

(56) References Cited

U.S. PATENT DOCUMENTS

| | | | |
|---|---|---|---|
| 5,990,681 A * | 11/1999 | Richard et al. | 324/318 |
| 7,538,552 B2 * | 5/2009 | Leussler | 324/318 |
| 7,755,357 B2 * | 7/2010 | Holle et al. | 324/318 |

* cited by examiner

*Primary Examiner* — Dixomara Vargas
(74) *Attorney, Agent, or Firm* — Ziolkowski Patent Solutions Group, SC

(57) ABSTRACT

An MRI apparatus and method is disclosed comprising a magnetic resonance imaging (MRI) system having a plurality of gradient coils positioned about a bore of a magnet, and an RF transceiver system and an RF switch controlled by a pulse module to transmit RF signals to an RF coil assembly to acquire MR images. The RF coil assembly comprises an RF tube, a plurality of electrically conductive members disposed around the RF tube and configured to transmit RF excitation pulses, a plurality of electrical components coupled to the electrically conductive members, and at least one thermally conductive substrate mounted upon the RF tube, wherein one of the plurality of electrically conductive members and the plurality of electrical components is mounted to the at least one thermally conductive substrate and is in thermal contact therewith.

20 Claims, 3 Drawing Sheets

RADIO FREQUENCY (RF) COIL FOR MRI HAVING HIGH THERMAL CONDUCTIVITY

BACKGROUND OF THE INVENTION

Embodiments of the invention relate generally to a radio frequency (RF) coil for use in an MR system and, more particularly, to an RF coil having improved thermal dissipation characteristics.

When a substance such as human tissue is subjected to a uniform magnetic field (polarizing field B0), the individual magnetic moments of the spins in the tissue attempt to align with this polarizing field, but precess about it in random order at their characteristic Larmor frequency. If the substance, or tissue, is subjected to a magnetic field (excitation field B1) which is in the x-y plane and which is near the Larmor frequency, the net aligned moment, or "longitudinal magnetization", MZ, may be rotated, or "tipped", into the x-y plane to produce a net transverse magnetic moment Mt. A signal is emitted by the excited spins after the excitation signal B1 is terminated and this signal may be received and processed to form an image.

When utilizing these signals to produce images, magnetic field gradients (Gx, Gy, and Gz) are employed. Typically, the region to be imaged is scanned by a sequence of measurement cycles in which these gradients vary according to the particular localization method being used. The resulting set of received NMR signals is digitized and processed to reconstruct the image using one of many well known reconstruction techniques.

Magnetic resonance imaging systems utilize at least one radio frequency (RF) coil that applies a high-frequency magnetic field over a subject and detects a magnetic resonance signal emitted from the subject. Such transmitting and receiving may be performed by a single RF coil or by separate coils, which perform the respective transmitting and receiving operations. The RF coil or coils themselves are formed of electrically conductive members connected to various electrical components, such as capacitors, diodes, inductors, etc. When an RF coil is pulsing during operation, these electrical components may generate a significant amount of heat. Extended pulsing of the RF coil may eventually lead to highly elevated temperatures under and around the electrical components, which can potentially lead to failure of these components and/or patient discomfort within the patient bore.

The elevated temperatures near the electrical components of the RF coil are also exacerbated by poor heat dissipation in the substrate upon which those electrical components are mounted. Conventionally, a G10 FR4 electrical insulation material is used to mount the electrical components, but this insulation material is not capable of effective heat dissipation at high temperatures and is thus prone to failure due to thermal stresses over time. Other methods of reducing heat caused by extended pulsing of the RF coil may include increasing the RF tube thickness on which the RF coil is assembled, increasing the air flow over the RF coil, or reducing the air inlet temperature around the RF coil. However, these alternative techniques involve either increasing the magnet bore size or implementing a larger heat exchanger into the MR system, both of which involve a significant design alteration to other MR subsystems (e.g., magnet and/or gradient coil) and are extremely cost prohibitive.

It would therefore be desirable to produce a system and method of manufacturing an MRI RF coil comprising a low cost substrate having high thermal conductivity upon which the electrical components of the RF coil can be mounted.

BRIEF DESCRIPTION OF THE INVENTION

Embodiments of the invention provide an MRI apparatus comprising a magnetic resonance imaging (MRI) system having a plurality of gradient coils positioned about a bore of a magnet, and an RF transceiver system and an RF switch controlled by a pulse module to transmit RF signals to an RF coil assembly to acquire MR images. The RF coil assembly comprises an RF tube, a plurality of electrically conductive members disposed around the RF tube and configured to transmit RF excitation pulses, a plurality of electrical components coupled to the electrically conductive members, and at least one thermally conductive substrate mounted upon the RF tube, wherein one of the plurality of electrically conductive members and the plurality of electrical components is mounted to the at least one thermally conductive substrate and is in thermal contact therewith.

In accordance with another aspect of the invention, a radio frequency (RF) coil for a magnetic resonance imaging system comprises an RF tube, a plurality of electrically conductive members disposed around the RF tube, and a plurality of electrical components coupled to the plurality of electrically conductive members. The RF coil further comprises at least one thermally conductive substrate mounted to the RF tube, wherein the plurality of electrical components is mounted to the at least one thermally conductive substrate, and wherein the at least one thermally conductive substrate has a thermal conductivity of at least 150 W/mK.

In accordance with another aspect of the invention, a method of manufacturing a radio frequency (RF) coil for use in a magnetic resonance imaging system is disclosed, the method comprising disposing an RF tube about a volume of the magnetic resonance imaging system, affixing at least one thermally conductive substrate to the RF tube, disposing a plurality of electrically conductive members having a plurality of electrical components connected thereto around the RF tube, and affixing at least one of the plurality of electrically conductive members and the plurality of electrical components to the at least one thermally conductive substrate.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION

A system is shown to dissipate heat in and around an RF coil of a magnetic resonance imaging (MRI) system using a highly thermally conductive substrate material, wherein components of the RF coil are mounted to the thermally conductive substrate.

Figure 1:
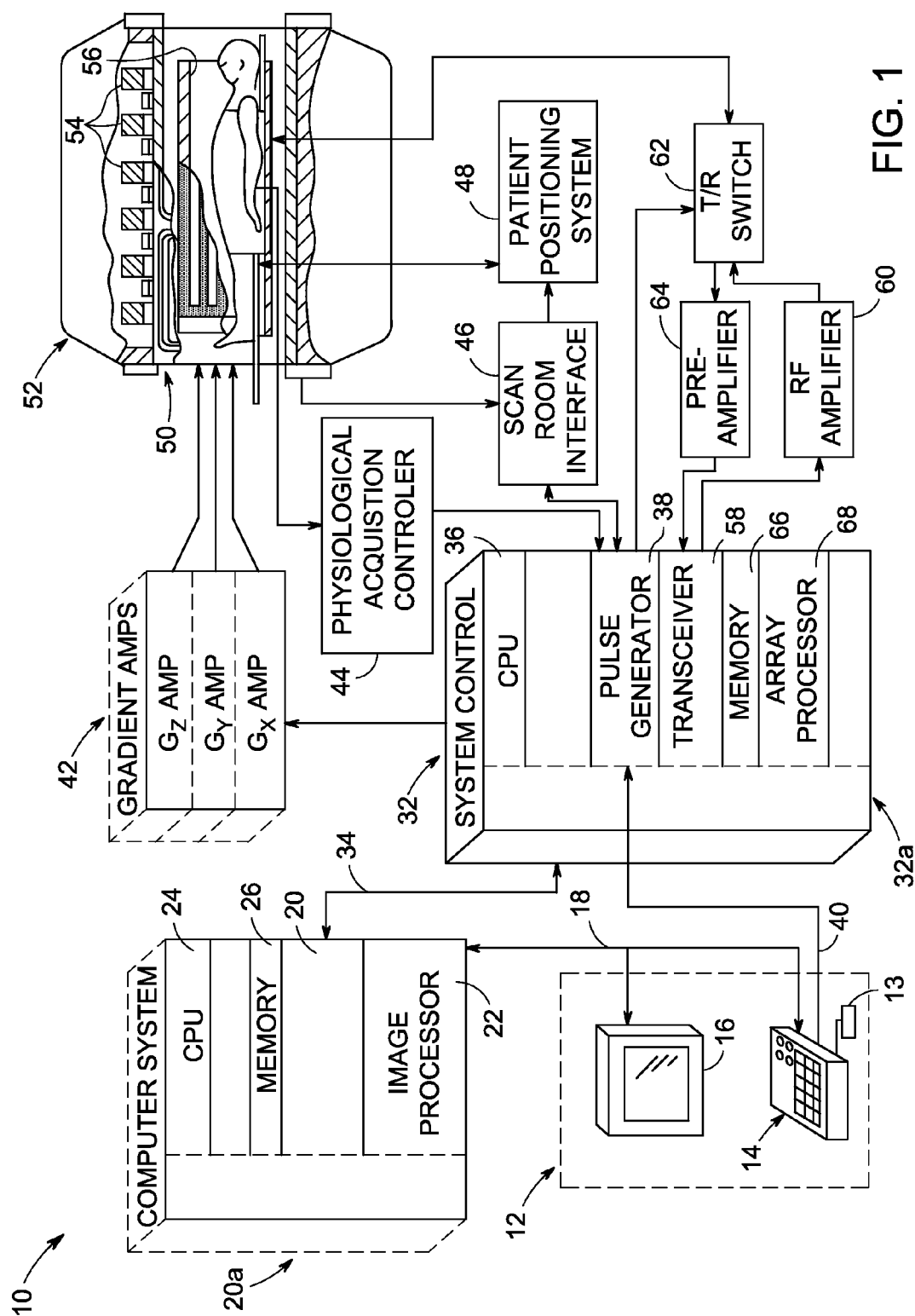
FIG. 1 is a schematic block diagram of an exemplary MR imaging system for use with an embodiment of the invention.

Referring to FIG. 1, the major components of a magnetic resonance imaging (MRI) system 10 incorporating an embodiment of the invention are shown. The operation of the system is controlled for certain functions from an operator console 12 which in this example includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These modules include an image processor module 22, a CPU module 24 and a memory module 26, known in the art as a frame buffer for storing image data arrays. The computer system 20 communicates with a separate system control 32 through a high speed serial link 34. The input device 13 can include a mouse, joystick, keyboard, track ball, touch activated screen, light wand, voice control, card reader, push-button, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having Gx, Gy, and Gz amplifiers. Each gradient amplifier excites a corresponding physical gradient coil in a gradient coil assembly generally designated 50 to produce the magnetic field gradients used for spatially encoding acquired signals. The gradient coil assembly 50 forms part of a resonance assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory. In response to commands received from the operator console 12 or as otherwise directed by the system software, this image data may be archived in long term storage or it may be further processed by the image processor 22 and conveyed to the operator console 12 and presented on the display 16.

During operation of the MRI system, extended pulsing of the RF coil causes substantial heat generation from various components of the RF coil. In particular, the electrical components of the RF coil (e.g., capacitors, inductors, diodes) generate heat during operation, thereby elevating the temperature of the regions surrounding those electrical components. Such elevated temperatures may potentially lead to failure of the components themselves or failure of the surrounding structures due to thermal stress. Furthermore, excess heat from the RF coil components may also increase the temperature within the patient bore of the MRI system, thereby reducing patient comfort. While certain materials generally separate the RF coil and related components from the patient bore, those materials generally have poor heat dissipation characteristics. Thus, there is a need for an RF coil having improved thermal characteristics, as will be described in further detail herein.

Figure 2:
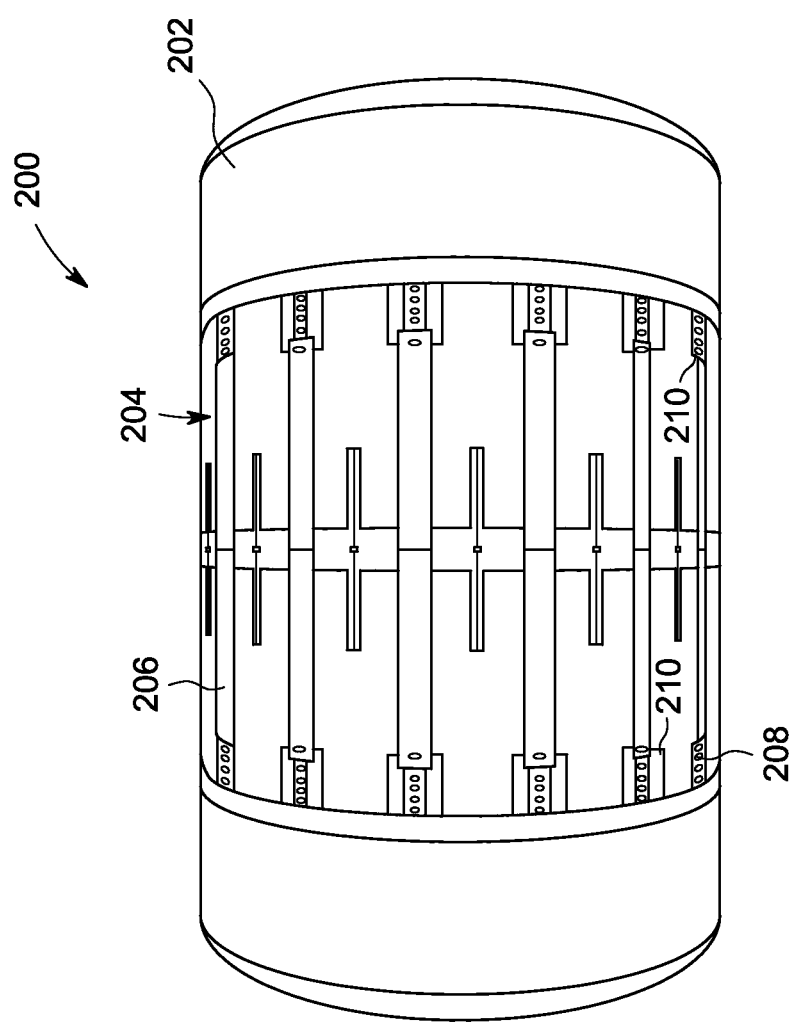
FIG. 2 is a side-view of an RF coil assembly in accordance with an embodiment of the invention.

Referring to FIG. 2, an RF coil assembly 200 in accordance with an embodiment of the invention is shown. RF coil assembly 200 comprises an RF tube 202, which encompasses the patient bore of the MRI system, as is the case with whole-body RF coil 56 shown in FIG. 1. Alternatively, RF coil assembly 200 could be configured as a head coil or other suitable RF coil for use in MRI applications. Surrounding RF tube 202 is an RF coil 204, which includes a plurality of electrically conductive members 206, as well as a plurality of electrical components 208 coupled to electrically conductive members 206. The plurality of electrically conductive members 206 are generally formed of copper, but may be made of other suitable electrically conductive material(s). The plurality of electrical components 208 of RF coil 204 may be any suitable devices, such as capacitors, diodes, inductors, etc. Electrical components 208 may be mounted to printed circuit boards (PCBs), which may themselves be coupled to electrically conductive members 206 of RF coil 204.

As current is applied to RF coil 204 during operation of the MR system, heat is generated by electrical components 208 and electrically conductive members 206 of RF coil 204. To enable dissipation of much of this heat at the areas surrounding RF coil 204, RF coil assembly 200 includes a plurality of thermally conductive substrates 210 placed between RF tube 202 and RF coil 204. As FIG. 2 shows, each of the plurality of electrical components 208 is mounted upon thermally conductive substrates 210, which are in turn mounted to RF tube 202, thereby creating a barrier between the heat-generating components of RF coil 204 and RF tube 202. Each thermally conductive substrate 210 is a polished substrate having a thermal conductivity value of at least 150 W/mK, which allows for efficient dissipation of heat from the plurality of electrical components 208 and electrically conductive members 206, while maintaining a relatively cool patient bore surface of RF tube 202. Thermally conductive substrates 210 may be formed of any suitable material having the above-described thermal conductivity characteristics, such as aluminum nitride. Moreover, thermally conductive substrates 210 may have a thickness of about 0.5 mm.

In addition to having high thermal conductivity characteristics, thermally conductive substrates 210 are also configured to have high electrical resistivity (greater than 1014 ohm-cm) and high dielectric breakdown voltage (greater than 15 kV/mm) to withstand excess voltage generated during RF transmission. Furthermore, thermally conductive substrates 210 are preferably formed of a flame retardant material. Using such thermally conductive substrates reduces the need for other forms of RF coil cooling and enables the RF tube to be thinner, which can improve the RF performance of the RF coil during operation.

Figure 3:
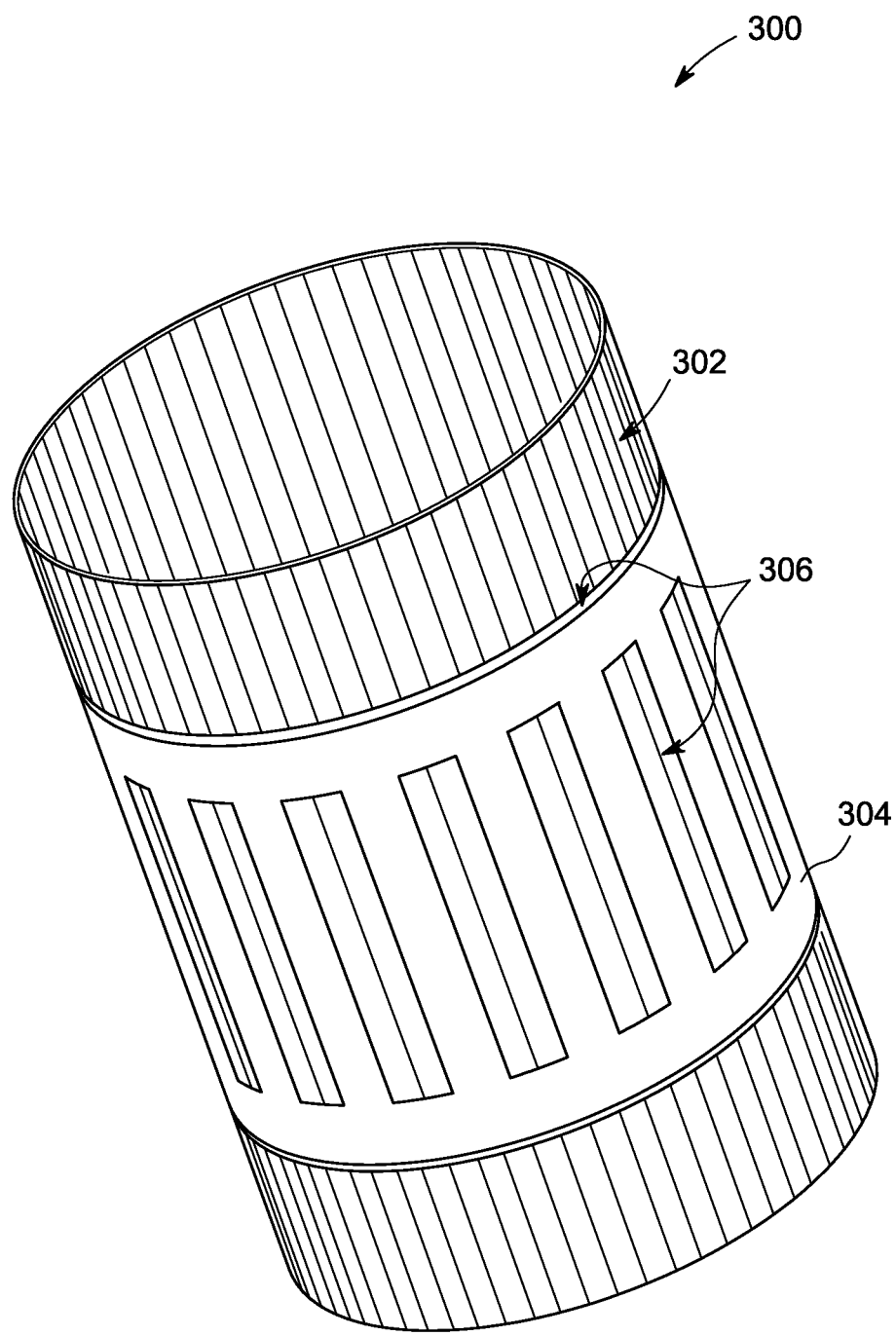
FIG. 3 is a perspective view of an RF coil assembly in accordance with an embodiment of the invention.

While RF coil assembly 200 shown in FIG. 2 comprises a plurality of thermally conductive substrates 210 affixed only at the locations of electrical components 208, embodiments of the invention are not limited as such. Referring to FIG. 3, an alternative embodiment of the invention is shown. FIG. 3 illustrates an RF coil assembly 300 comprising an RF tube 302, RF coil 304, and a thermally conductive substrate 306 affixed to a surface of RF tube 302 between RF tube 302 and RF coil 304. Although not explicitly shown in FIG. 3, it is to be understood that RF coil 304 comprises a plurality of electrical components and a plurality of electrically conductive members similar to those shown with respect to FIG. 2. Unlike RF coil assembly 200 shown in FIG. 2, thermally conductive substrate 306 is not limited solely to locations adjacent to the electrical components of RF coil 304, but may also be disposed adjacently to and thermally coupled to the entirety of RF coil 304. Such a configuration enables additional heat dissipation around all components of RF coil 304, not only the regions where electrical components (e.g., capacitors, inductors, etc.) of RF coil 304 are located. In yet another embodiment not illustrated in FIG. 3, the thermally conductive substrate may alternatively be affixed only at the points on the RF tube where the electrical components and electrically conductive members of the RF coil are disposed, thereby reducing the amount of material used in forming the thermally conductive substrate while still maintaining substantial heat dissipation.

Unlike other possible substrate materials, the highly thermally conductive substrate described with respect to FIG. 2 and FIG. 3 effectively dissipates heat emitted from the RF coil components to reduce the likelihood of component failure and to increase patient comfort within the patient bore of the MRI system. For example, during pulsing of the RF coil for 70 seconds, other substrate materials having an initial ambient temperature may reach a much higher temperature that result in material failure of the substrate and excessive heating of the RF tube. Conversely, under similar pulsing of the RF coil for 70 seconds, the thermally conductive substrate material of the invention may reaches a much lower maximum temperature that result in no material damage to the substrate or the surrounding components. Accordingly, the thermally conductive substrate of the invention efficiently dissipates heat away from the RF coil and related components without adding substantial heat to the RF tube and without adding electrical conductivity to the heated regions.

While the embodiments described with respect to FIG. 2 and FIG. 3 only involve the use of the thermally conductive material as a substrate to the RF coil and related components, embodiments of the invention are not limited as such. For example, in another embodiment, the rung, end-ring, and decoupling PCBs of an RF coil may be manufactured using the same highly thermally conductive material. Also, dielectric board capacitors or distributed capacitors (double-sided PCBs) of the RF coil may be made using the highly thermally conductive material. Additionally, the RF tube itself may be covered with (or constructed of) the highly thermally conductive material, thereby making the RF coil assembly entirely flame retardant.

Previous methods of reducing heating in and around the RF coil of MRI systems have included increasing the thickness of the RF tube on which the RF coil is assembled, increasing the air flow to the RF coil, and/or reducing the air inlet temperature to the RF coil. However, these heat dissipation techniques necessitate either increasing the size of the magnet bore or implementing a larger heat exchanger into the MR system, which in turn involves significant design alterations to other MR subsystems (e.g., magnet and/or gradient coils) and adds significant cost to the system. Through the use of the thermally conductive substrate of the invention, heat dissipation around the RF coil is achieved at a low cost and with little to no alterations to other existing MR subsystems.

Therefore, an embodiment of the invention provides an MRI apparatus comprising a magnetic resonance imaging (MRI) system having a plurality of gradient coils positioned about a bore of a magnet, and an RF transceiver system and an RF switch controlled by a pulse module to transmit RF signals to an RF coil assembly to acquire MR images. The RF coil assembly comprises an RF tube, a plurality of electrically conductive members disposed around the RF tube and configured to transmit RF excitation pulses, a plurality of electrical components coupled to the electrically conductive members, and at least one thermally conductive substrate mounted upon the RF tube, wherein one of the plurality of electrically conductive members and the plurality of electrical components is mounted to the at least one thermally conductive substrate and is in thermal contact therewith.

In accordance with another aspect of the invention, a radio frequency (RF) coil for a magnetic resonance imaging system comprises an RF tube, a plurality of electrically conductive members disposed around the RF tube, and a plurality of electrical components coupled to the plurality of electrically conductive members. The RF coil further comprises at least one thermally conductive substrate mounted to the RF tube, wherein the plurality of electrical components is mounted to the at least one thermally conductive substrate, and wherein the at least one thermally conductive substrate has a thermal conductivity of at least 150 W/mK.

In accordance with another aspect of the invention, a method of manufacturing a radio frequency (RF) coil for use in a magnetic resonance imaging system is disclosed, the method comprising disposing an RF tube about a volume of the magnetic resonance imaging system, affixing at least one thermally conductive substrate to the RF tube, disposing a plurality of electrically conductive members having a plurality of electrical components connected thereto around the RF tube, and affixing at least one of the plurality of electrically conductive members and the plurality of electrical components to the at least one thermally conductive substrate.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An MRI apparatus comprising:
a magnetic resonance imaging (MRI) system having a plurality of gradient coils positioned about a bore of a magnet, and an RF transceiver system and an RF switch controlled by a pulse module to transmit RF signals to an RF coil assembly to acquire MR images, wherein the RF coil assembly comprises:
an RF tube;
a plurality of electrically conductive members disposed around the RF tube and configured to transmit RF excitation pulses;
a plurality of electrical components coupled to the electrically conductive members; and
at least one thermally conductive substrate mounted upon the RF tube, wherein one of the plurality of electrically conductive members and the plurality of electrical components is mounted to the at least one thermally conductive substrate and is in thermal contact therewith.

2. The MRI apparatus of claim 1 wherein the thermally conductive substrate has a thermal conductivity of at least 150 W/mK.

3. The MRI apparatus of claim 1 wherein the plurality of electrical components are selected from the group consisting of capacitors, diodes, and inductors.

4. The MRI apparatus of claim 1 wherein the at least one highly thermally conductive substrate is formed of a material having an electrical resistivity greater than $10^{14}$ ohm-cm and a dielectric breakdown voltage greater than 15 kV/mm.

5. The MRI apparatus of claim 1 wherein the at least one thermally conductive substrate is formed of a material that is flame-retardant.

6. The MRI apparatus of claim 1 wherein the at least one thermally conductive substrate is formed of aluminum nitride.

7. The MRI apparatus of claim 1 wherein the at least one thermally conductive substrate has a thickness of at least 0.5 millimeters.

8. The MRI apparatus of claim 1 wherein at least one of the plurality of electrical components is formed of a thermally conductive material.

9. The MRI apparatus of claim 1 wherein the RF tube is formed of aluminum nitride.

10. The MRI apparatus of claim 1 wherein the RF coil is one of a whole-body coil and a head coil.

11. A radio frequency (RF) coil for a magnetic resonance imaging system, the RF coil comprising:
an RF tube;
a plurality of electrically conductive members disposed around the RF tube;
a plurality of electrical components coupled to the plurality of electrically conductive members; and
at least one thermally conductive substrate mounted to the RF tube, wherein the plurality of electrical components is mounted to the at least one thermally conductive substrate, and wherein the at least one thermally conductive substrate has a thermal conductivity of at least 150 W/mK.

12. The RF coil of claim 11 wherein the RF coil is a whole-body coil.

13. The RF coil of claim 11 wherein the RF coil is a head coil.

14. The RF coil of claim 11 wherein the at least one thermally conductive substrate is formed of aluminum nitride.

15. The RF coil of claim 11 wherein the at least one thermally conductive substrate is formed of a flame-retardant material.

16. The RF coil of claim 11 wherein the RF tube is formed of a thermally conductive material.

17. The RF coil of claim 11 wherein at least one of the plurality of electrical components is formed of a thermally conductive material.

18. A method of manufacturing a radio frequency (RF) coil for use in a magnetic resonance imaging system, the method comprising:
disposing an RF tube about a volume of the magnetic resonance imaging system;
affixing at least one thermally conductive substrate to the RF tube;
disposing a plurality of electrically conductive members having a plurality of electrical components connected thereto around the RF tube; and
affixing at least one of the plurality of electrically conductive members and the plurality of electrical components to the at least one thermally conductive substrate.

19. The method of claim 18 wherein the step of affixing the at least one thermally conductive substrate to the RF tube comprises affixing the at least one thermally conductive substrate only at RF tube locations upon which the plurality of electrical components are to be mounted.

20. The method of claim 18 further comprising forming the at least one thermally conductive substrate of aluminum nitride.

* * * * *